(12) United States Patent
Bolla (10) Patent No.: US 9,039,643 B2
(45) Date of Patent: May 26, 2015

(54) FASTENING ELEMENT, USE OF THE ELEMENT FOR IMMOBILIZING OBJECT, PREFERABLY PARTS OF THE BODY AND DEVICE CONTAINING THE ELEMENT

(75) Inventor: Kalman Bolla, Neuhausen am Rheinfall (CH)

(73) Assignee: CHRISOFIX AG, Neuhausen am Rheinfall (CH)

( * ) Notice: Subject to any disclaimer, the term of this patent is extended or adjusted under 35 U.S.C. 154(b) by 214 days.

(21) Appl. No.: 13/497,496

(22) PCT Filed: Sep. 8, 2010

(86) PCT No.: PCT/EP2010/063144
§ 371 (c)(1),
(2), (4) Date: Jul. 23, 2012

(87) PCT Pub. No.: WO2011/036054
PCT Pub. Date: Mar. 31, 2011

(65) Prior Publication Data
US 2013/0035621 A1 Feb. 7, 2013

(30) Foreign Application Priority Data

Sep. 22, 2009 (CH) ........................................ 1459/09
Feb. 12, 2010 (CH) ........................................ 0177/10

(51) Int. Cl.
*A61F 5/00* (2006.01)
*A61F 5/058* (2006.01)

(52) U.S. Cl.
CPC ......... *A61F 5/05825* (2013.01); *A61F 5/05841* (2013.01)

(58) Field of Classification Search
CPC ................ A61M 16/0683; A61M 16/0875; A61M 2209/088; A61B 17/0401; A61B 2017/0464; A61B 2017/0409; A61B 2017/0437; A61B 17/0057; A61B 17/0466; A61B 17/0487; A61B 17/06166; A61B 17/064
USPC ........... 602/5, 6, 8, 20–28; 128/878–879, 882
See application file for complete search history.

(56) References Cited

U.S. PATENT DOCUMENTS

| | | | | |
|---|---|---|---|---|
| 2,273,028 A * | 2/1942 | Eaton | ............................. | 602/22 |
| 2,667,808 A * | 2/1954 | Hart | ............................. | 352/174 |
| 3,850,167 A * | 11/1974 | Seeley | ............................. | 602/6 |
| 4,161,175 A * | 7/1979 | Bentele | ............................. | 602/6 |
| 6,039,706 A * | 3/2000 | Bolla et al. | ....................... | 602/5 |
| 7,329,229 B2 * | 2/2008 | Scheinberg et al. | ............. | 602/5 |
| 2007/0197945 A1 * | 8/2007 | Islava | ............................. | 602/24 |
| 2008/0249445 A1 * | 10/2008 | Bailey | ............................. | 602/6 |

* cited by examiner

*Primary Examiner* — Michael Brown
(74) *Attorney, Agent, or Firm* — Dowell & Dowell, PC (57) ABSTRACT

The invention relates to a fixing element (33) extending as a flat, particularly lamellar element along a preferred direction (34) and comprising a corrugated sheet metal core (18) as a central component, said core providing the fixing element (33) with the characteristic of being integrally rigid and permanently deformable by hand, and said core being covered by a cover (36, 37). For such a fixing element, a large range of use is achieved in that the corrugations of the corrugated core sheet (18) are oriented substantially parallel to the preferred direction (34), and that means (38, 39) for releasably attaching the fixing element (33) are disposed on the fixing element (33).

10 Claims, 7 Drawing Sheets

FASTENING ELEMENT, USE OF THE ELEMENT FOR IMMOBILIZING OBJECT, PREFERABLY PARTS OF THE BODY AND DEVICE CONTAINING THE ELEMENT

The present invention generally relates to the field of fastening techniques, and in particular to a fastening element, for example for medical splints.

BACKGROUND ART

The document WO 9722312 A1 discloses a medical splint, the main feature of which is that it contains a core sheet, which may be plastically deformed by hand, without using auxiliary tools. The core sheet is a metal plate which is provided with corrugations, wherein ribs and channels are arranged substantially transverse to a particular direction, namely the longitudinal axis of the splint.

The corrugated core sheet, which is preferably made of aluminum and has a thickness of, for example 0.2 to 0.4 mm, is covered on both sides with a layer, which is adapted to the particular application. The inner covering layer may be formed as a cushion in order to improve the wearing comfort of the splint's rail. The outer covering layer may be washable, in order to make the splint less sensitive to external influences.

The basic idea of this type of splint is that the corrugation of the core sheet provides a "reserve area" which facilitates the adjustment of the splint on irregular body shapes. During shaping the splint itself by hand, the corrugations can be pressed locally to be flat or erected, which allows a local expansion or contraction of the splint.

In this way, wrinkling or buckling of the plate—as would be expected during the deformation of a flat plate—may be avoided. In addition, as a result of the arrangement of the corrugations transverse to the longitudinal direction of the splint during shaping the splint to fit to the splinted body part, a stiffening of the whole splint is achieved, so that it will have almost ideal properties for quick and easy manipulation, in order to be adapted to the shape of the splinted body part, for easy and comfortable wearing, and for providing the desired high rigidity.

Up to now, resilient and flexible, mostly textile-like straps have been applied for fixing a medical splint to an injured body part. These straps, however, did not sufficiently restrict the movement of the splinted body part. In some cases, however, it is desirable to apply fastening straps with which the splinting effect can be enhanced, and which can be also used for different purposes beyond the medical field.

The document U.S. Pat. No. 3,850,167 also discloses a medical splint comprising two corrugated core sheets, wherein the splint is to be tensioned around a body part along a direction transverse to the longitudinal direction of the splint.

It is therefore an object of the invention to provide an improved fastening element, especially for medical splints, but also for use in other fields, such as packaging objects, which elements may be deformed easily without any auxiliary tool and provide accurate and reliable fixation. It is another object of the invention to provide a method of immobilizing a body part by using such a fastening element. It is yet another object of the invention to provide a device for immobilizing an object.

SUMMARY OF THE INVENTION

These and other objects of the invention are achieved by providing a fastening element formed as a flat, elongated strap and comprising a rigid, yet manually deformable, corrugated metal plate, said fastening element having a longitudinal axis and two longitudinally opposite end portions, said longitudinal axis extending in a direction along which the fastening element is to be tensioned onto or around an object, wherein the corrugations of the metal plate are arranged substantially parallel to the longitudinal axis of the fastening element, and wherein the corrugated metal plate is provided on both faces thereof with an external covering layer and at least at its longitudinally opposite end portions, with means for releasably attaching the fastening element on or around said object.

Preferably, the corrugated plate is made of aluminium.

Preferably, the corrugated plate has a thickness of 0.2-1.2 mm.

Preferably, the attaching means include hook and loop fasteners.

It is also preferred that the external covering layers are made of a flexible material selected from the group of textile and foam.

The above objects are further achieved by providing a method of immobilizing a body part by using a fastening element, wherein the fastening element is formed as a flat, elongated strap and comprises a rigid, yet manually deformable, corrugated metal plate, said fastening element having a longitudinal axis and two longitudinally opposite end portions, said longitudinal axis extending in a direction along which the fastening element is to be tensioned onto or around an object, wherein the corrugations of the metal plate are arranged substantially parallel to the longitudinal axis of the fastening element, and wherein the corrugated metal plate is provided on both faces thereof with an external covering layer and at least at its longitudinal end portions, with means for releasably attaching the fastening element on or around said object, the method comprising:

winding said fastening element around a body to form a helical winding for fixing the body in place Preferably, the helically wound fastening element is held in a predetermined configuration by reinforcing elements applied externally on the helical winding.

Preferably, the body is a finger and the fastening element is helically wound around the finger.

The above objects are also achieved by providing a device comprising a stable support for holding an object and at least one fastening element, wherein said at least one fastening element is formed as a flat, elongated strap and comprises a rigid, yet manually deformable, corrugated metal plate, and further has a longitudinal axis and two longitudinally opposite end portions, said longitudinal axis extending in a direction along which the fastening element is to be tensioned onto or around said stable support, wherein the corrugations of the metal plate are arranged substantially parallel to the longitudinal axis of the fastening element, wherein the corrugated metal plate is provided on both faces thereof with an external covering layer and at least at its longitudinally opposite end portions, with means for releasably attaching the fastening element to said support for immobilizing the object held by the support, and wherein said support comprises counterpart attaching means adapted for coupling with the attaching means of the at least one fastening element.

Preferably, the support is a medical splint.

BRIEF DESCRIPTION OF THE DRAWINGS

The invention will be explained in more detail with reference to the accompanying drawings, wherein.

DETAILED DESCRIPTION OF THE PREFERRED EMBODIMENTS OF THE INVENTION

FIGS. 2, 4, 7 and 8 show various embodiments of the fastening element according to the invention. Fastening elements 13 and 13' of FIGS. 2 and 4 will be explained further below, in connection with the use of the fastening element in a device 10 shown in FIG. 1 and for an elbow splint 22 shown in FIG. 3. It is obvious for those skilled in the art that other applications of the fastening element of the invention within the scope of the invention are also possible and may be advantageous.

Figure 3:
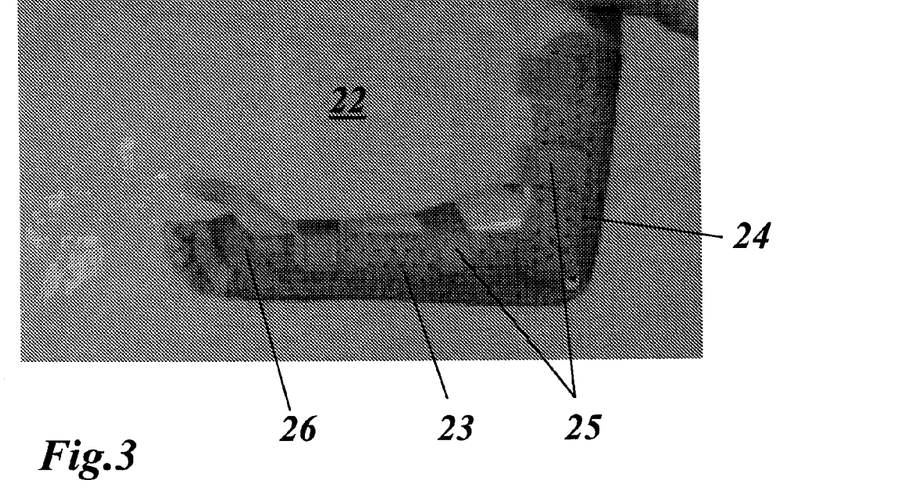
FIG. 3 shows an elbow splint known in the art, provided with flexible fastening elements.

FIG. 3 shows an elbow splint known in the art. The elbow splint 22 comprises a lower arm part 23 and an upper arm part 24, arranged at about a right angle relatively to each other. Both parts 23, 24 have a U-shaped cross-section that accommodates the forearm and upper arm almost completely. For fixing the elbow splint 22 around the arm, a plurality of flexible straps 25 according to the prior art are removably fixed on both sides of the splint to keep the arm immobilized.

The elbow splint 22 may be covered on the inside to provide wearing comfort for the patient, and may be perforated to allow air flow to the arm in the splint.

A critical part of the known elbow splint 22 is the leading end portion in which the hand rests. The hand is positioned substantially vertically in the splint and is immobilized therein by a long strap 26 that passes between the thumb and the forefinger. Since this long strap 26 is also flexible, the immobilization effect is insufficient for several reasons, for example the hand can turn around its longitudinal axis in spite of the long strap 26, which can be dangerous in certain injury situations of the arm and which, anyway, reduces more or less the immobilizing effect of the splint.

Figure 2:
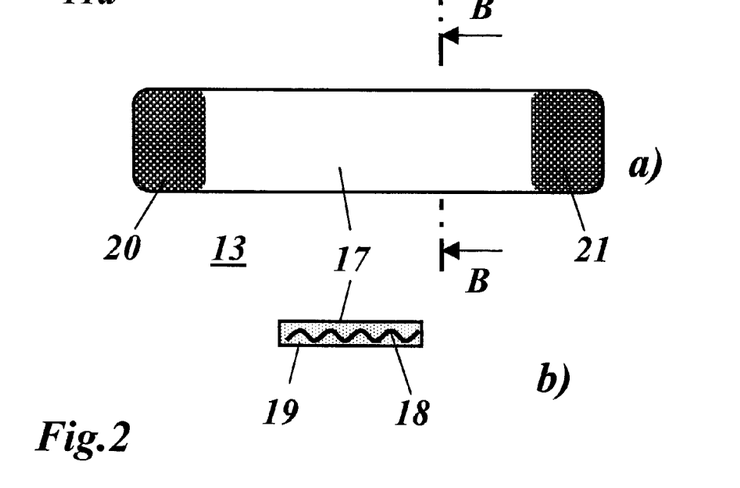
FIG. 2a is a top view of a preferred embodiment of the invention.
FIG. 2b shows the cross-section of the fastening element shown in FIG. 2a along the line B-B

To overcome this problem, the object of the invention is to provide rigid and effective fastening elements instead of the conventional flexible straps 25 and 26 The fastening element 13 shown in FIG. 2 offers special deformation and stability properties, which are based on a corrugated metal plate 18, preferably made of aluminum, as it was already proposed for use as a splint material in the document WO 9722312 A1. The content of this documents is referred to in respect of the preferred dimensions and other advantageous characteristics of the corrugated core plate 18. However, unlike in the splint material introduced in the above document, the corrugations of the fastening element of the present invention do not extend transverse to the longitudinal direction of the fastening element, but they extend in parallel thereto, which corresponds to the tensioning direction 34 shown in FIG. 7. This arrangement provides improved properties for the fastening element 13. With a suitable thickness, the core metal plate 18 can be shaped manually without using any special auxiliary tool, wherein the height of the ribs may be increased by local compression, or reduced by local stretching of the fastening element in a direction transverse to its longitudinal tensioning direction 34. In this manner, the corrugated metal core plate 18 may be adjusted to any uneven shape without losing its rigidity. At the same time, due to the deformation of the ribs or waves, the stiffness of the material increases so that it can provide an even better supporting function. Additionally, the orientation of the ribs running in parallel to the longitudinal tensioning direction 34 ensure that no stretching or compression of the core plate 18 in this direction, and accordingly, no change in the length of the fastening element can occur.

Figure 5:
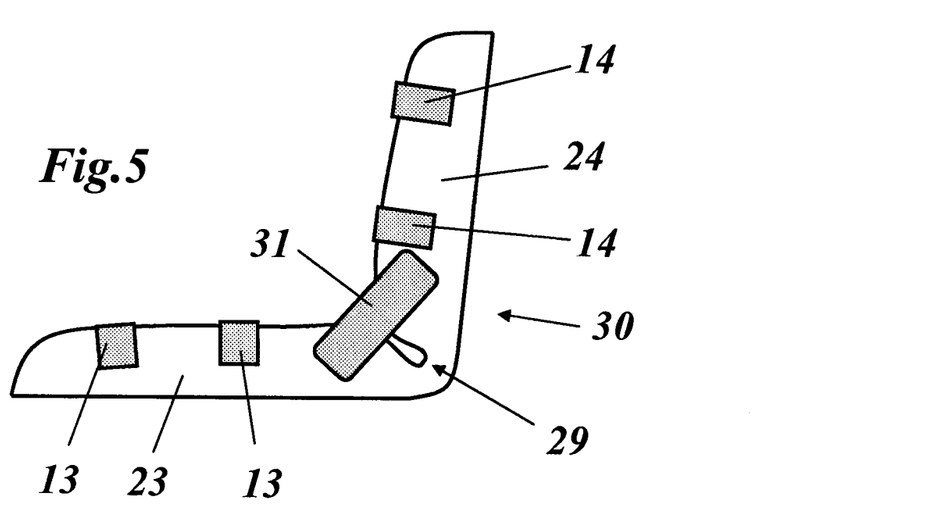
FIG. 5 shows an elbow splint provided with a number of fastening elements of the invention in a first arrangement.
Figure 6:
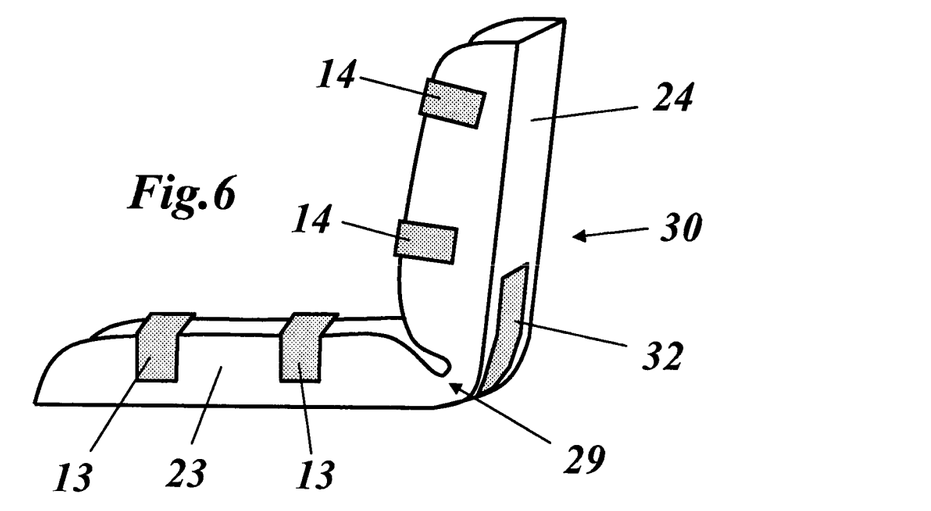
FIG. 6 shows an elbow splint provided with a number of fastening elements of the invention in a second arrangement.

When instead of the flexible fastening elements 26 shown in FIG. 3, fastening elements 13 according to the invention are applied on an elbow splint 30 as shown FIGS. 5 and 6) or on any other kind of splint, it can be adjusted to the hand in the position shown, and it is capable of holding the hand firmly in its position due to the rigidity of the core plate 18. Any accidental, harmful twisting of the hand is no longer possible.

Figure 4:
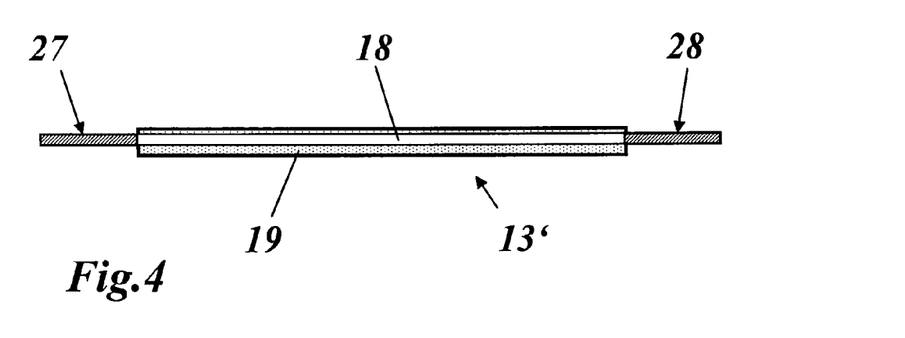
FIG. 4 shows a longitudinal section of another preferred embodiment of the fastening element according to the invention.

If such a fastening element is used with a medical splint, it is advantageous that the fastening element 13 is covered on one or both sides with a covering layer 19, which prevents the core plate 18 from directly contacting with the skin, as shown in FIG. 4. The material of the covering layer may be, for example, a foam or a textile tissue. Moreover, the fastening element 13, 13' may be perforated to allow air flow to the covered body parts.

Figures 7, 8:
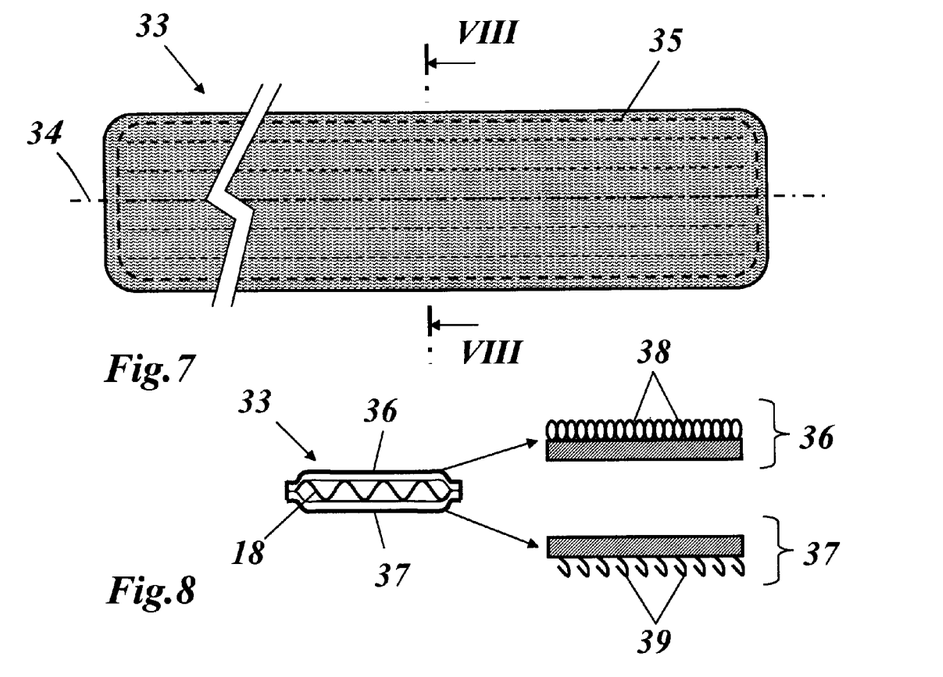
FIG. 7 is the top plan view of another embodiment of the fastening element according to the invention, which is covered over its entire surface with releasable attaching means in the form of hook and loop fasteners.
FIG. 8 is a cross-sectional view of the fastening element show in FIG. 7, wherein the hook and loop fasteners are shown separately in an enlarged view.

For a releasable attachment of the fastening element 13, 13' to a splint, the fastening element 13, 13' of the invention is provided at least at its two longitudinally opposite ends with attaching means 20, 21, preferably in the form of hooks 39 on one face of the fastening element and loops 38 on the other face of the fastening element as shown in FIG. 8. A particularly flexible splinting system can be constructed by providing the entire outer surface of the splint with hooks or loops, whereby the fastening elements may be secured to any part of the outer surface of the splint.

Instead of an integrated a hook and loop fastener system, the fastening element 13' may have other kind of attaching means 27, 28 as shown in FIG. 4. In this embodiment, the attaching means 27, 28 are formed as a flexible, preferably non-stretchable straps at the ends of the fastening element and hooks, snaps, or other releasable connecting means may be provided for securing the fastening element. It is also possible to stick the fastening element by a solvable (or unsolvable) glue to the splint. The fastening element and the splint may have a one-piece design, however, that has the disadvantage that relatively much material is lost when such an integrated device is cut to the desired shape.

It is obvious that fastening elements 13, 13' shown in FIGS. 2 and 4 may be used not only with an elbow splint as shown in FIGS. 5 and 6, but with any other medical splint, wherein a stable and accurate fastening of a splinted body part in or on a base element or support is to be achieved easily and reliably. A particular reference is made to an upper arm splint wherein the combination of a splint-like base and a plurality of fastening elements according to the invention enables that the upper arm splint may be used with a high wearing comfort by being adjusted to the particular shape of the upper arm in so manner that the splint cannot slip relative to the arm and at the same time, sufficient room is provided for the arm to move.

The fastening elements according to the invention, when used with medical splints, offer the advantage of being suitable for all kinds of splints due to the great number of different forms and core plate thicknesses. The splints may also be of different configurations, such as U-shaped base splint, semi-circular splint or a splint being entirely circular in those regions where the fastening elements are applied. In any case, the invented solution offers a high adaptability and a high wearing comfort.

Moreover, as it is shown with respect to the elbow splint 30 in FIGS. 5 and 6, additional fastening elements 31, 32 may be also used for fixing the elbow splint 30 (or other splints) in a certain (e.g. angular) configuration. The fastening elements 31, 32 are constructed similarly to the fastening elements 13, 13', and therefore they have similar rigidity and tensile strength in the longitudinal direction of the element. If the elbow splint 30 of FIG. 5 is bent in a bending region 29 at about right or other angle, this angular position may be stabilized simply by securing a rigid fastening element 31 to the splint 30 laterally, obliquely over the angular range, in order to prevent a change in the angle of the bending region 29. The fastening element 31 can be mounted either on only one side or on both sides of the splint 30.

An elbow splint 30 as shown in FIG. 6 or other splints may be stabilized by applying a fastening element 32 for external use, when in certain situations, the inherent stiffness of the splint material is not sufficient. Such external stabilizing is carried out preferably in a bending region 29, as shown in FIG. 6. However, it can be used on other locations of a more heavily loaded splint as well. In such cases, fastening elements with greater thickness—in the range from 0.6 mm to 1, 2 mm—should be applied.

Figure 1:
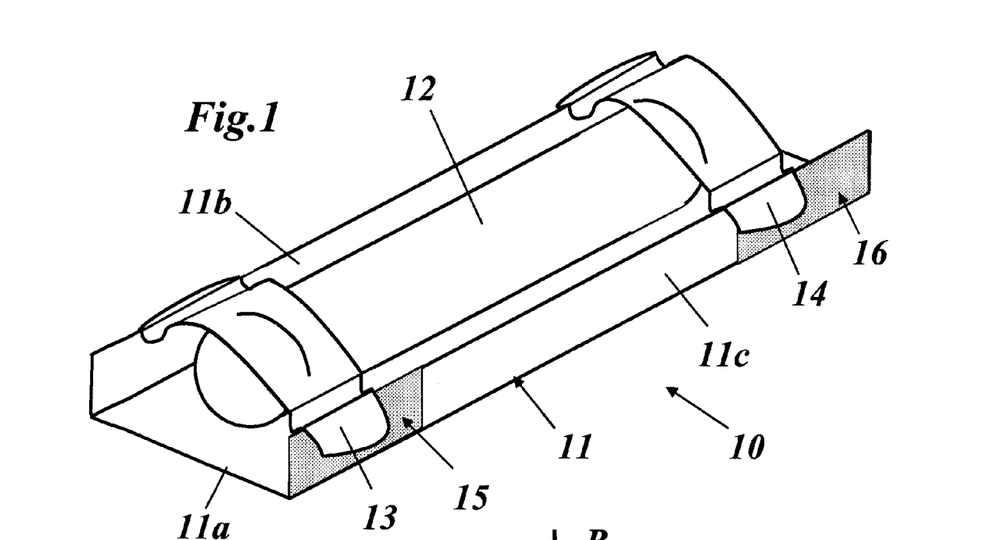
FIG. 1 is a perspective view of fastening elements according to the invention, wherein the fastening elements are tensioned around a support carrying an object.

The invention may also be generally used, however, beyond the field of medical splints, where an object of any shape should be fastened quickly and safely on a stable base or support. Such a universal embodiment is shown in FIG. 1. An object 12, having a cylindrical shape in this example, is arranged on a support 11 having a base 11a and two side walls 11b and 11c. Said object 12 should be fastened on the support 11 in a way to prevent its movement (rolling or sliding) with respect to the support 11. The end portions of the object 12 are therefore fastened with two strap-like fastening elements 13 and 14 according to the invention. The fastening elements 13, 14 are fitted to the circular contour of the object 12 and to the side walls 11b and 11c of the support 11. In order to keep the fastening elements 13 and 14 in place, the outer surface of the side walls 11b and 11c are provided with special regions 15, 16, which may have small loops, to which hooks of the attaching means formed on the fastening elements 13 and 14 may be connected. Any other way of fastening, removable or not removable, may be applied as well.

Due to the inherent rigidity of the fastening elements according to the invention, provided with a corrugated metal core plate, heavy objects can be immobilized on a support to avoid sliding or rolling of the object relatively to the support itself, wherein the shape of the fastening elements may be simply manually fitted to the shape of the object without using any auxiliary tool.

Especially extensive use can be made of the fastening element 33 shown in FIGS. 7 and 8. In this embodiment, both sides of the fastening element 33 are provided with covering layers 36 and 37 that have hooks and loops, respectively, on their entire outer surface. For example, the covering layer 36 may contain loops 38, meanwhile the outer surface of the other covering layer 37 may be provided with corresponding hooks 39. The covering layers 36 and 37 are connected to each other along their periphery, for example, by an edge seam 35 to form together a closed bag containing the corrugated core plate 18, wherein the corrugations are arranged in parallel with the longitudinal tensioning direction 34 of the fastening element 33, indicated in FIG. 7 by dotted lines.

Figure 9:
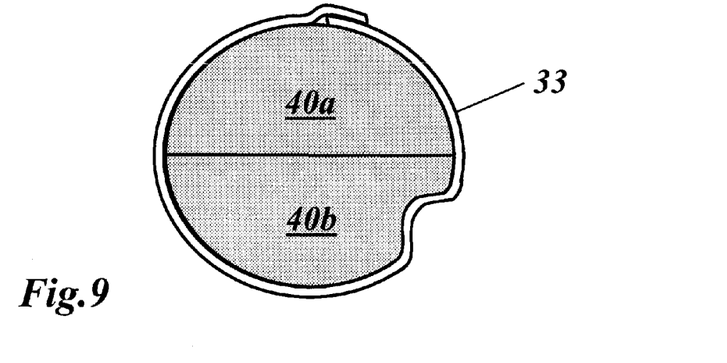
FIG. 9 is a cross-sectional view of a body part surrounded by a fastening element according to the invention.

The fastening element according to the invention can be used as shown in FIG. 9, wherein a body formed of two parts 40a and 40b is looped around with a fastening element 33. Due to its special properties, the fastening element 33 fits perfectly to the contours of the body, i.e. it matches the recesses or projections of the body. Especially high fastening may be achieved, if the external surface of body parts 40a and 40b have small loops or hooks, meanwhile the inner surface of the fastening element 33 has counterpart loops or hooks, thus providing in this way a releasable, but safe immobilizing of the joined body parts 40a and 40b.

Figure 10:
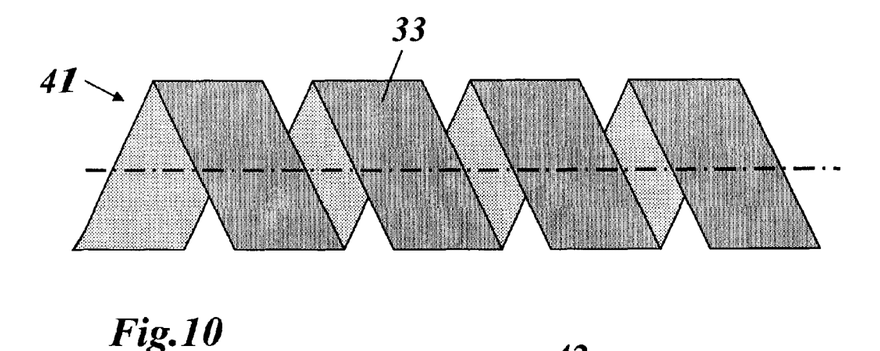
FIG. 10 illustrates the fastening element of the invention in a helically bent configuration adapted for immobilizing a body part (not shown) by wrapping around the body part along a winding axis.
Figure 11:
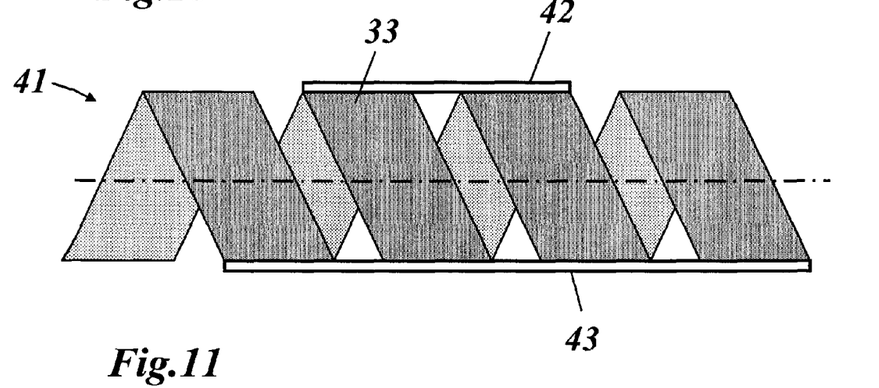
FIG. 11 shows the fastening element of FIG. 10 further provided with additional external reinforcing elements.
Figure 12:
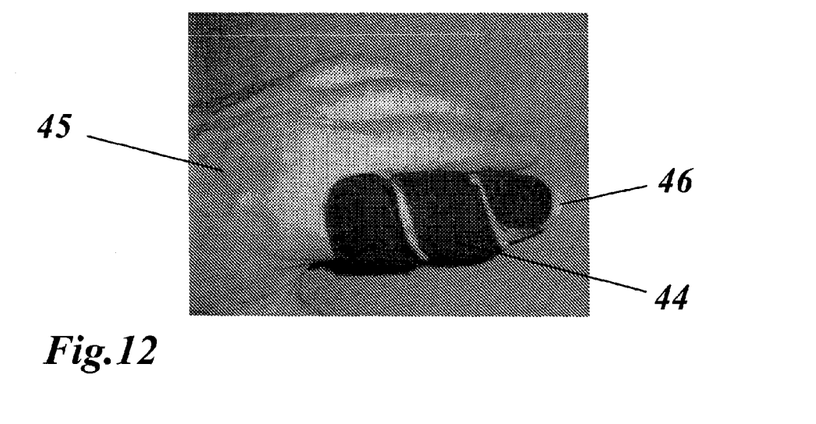
FIG. 12 shows the use of the fastening element according to the invention for the immobilization of a finger.

If the fastening element 33 is formed as a relatively long strip, it can be used in a particularly simple and effective way as a fixing bandage, as shown in FIGS. 10, 11 and 12. As shown in FIG. 10, the fastening element 33 may be wound around a body part (not shown), e.g. a forearm or a lower leg or a finger (see FIG. 12), and is, in this way, fitted to the shape of the wound body part. As a result the fastening element 33 forms a helical winding 41, which is relatively stable in shape, due to the core plate 18, but may be slightly bent and compressed together or pulled apart in the longitudinal direction of the helical winding 41. The dimensional stability also depends considerably on the thickness used and is particularly high when a thickness of about 1 mm is used. On the contrary, where an increased degree of deformability is required, a thickness of the metal core plate ranging from 0.2 mm to 0.4 mm is advantageous. Preferably no gap is left between the turns of the helical winding 41 in use.

If good plasticity should be combined with a high dimensional stability, it is advisable to choose smaller thicknesses and either overlapping and the turns of the helical winding and attaching the turns to each other, or applying additional reinforcing elements 42, 43 on the outside of the helical winding 41 as shown in FIG. 11. The reinforcing elements 42, 43 are arranged along the direction of the winding axis, and maintain the spacing between the winding turns constant to fix the shape of the fastening element.

FIG. 12 shows finally the application of a helically wound fastening element 44 as a light splinting of an index finger 46 of a hand 45. The movement of the finger 46 can in this way be restricted in the desired manner. By the use of additional fastening elements (not shown in FIG. 12), such as one or more straps with hooks and loops, the fastening element 44 may be stiffened in the longitudinal direction similarly to the use of the reinforcing elements shown in FIG. 11. It is also possible to connect the fastening element 44 to a wrist or forearm splint, by means of an additional fixing member, to immobilize the wrapped finger relative to the hand or forearm.

The strong immobilizing effect of the fastening element according to the invention applied with medical splints, as shown, for example, in FIGS. 5 and 6, was also tested experimentally.

Figure 13:
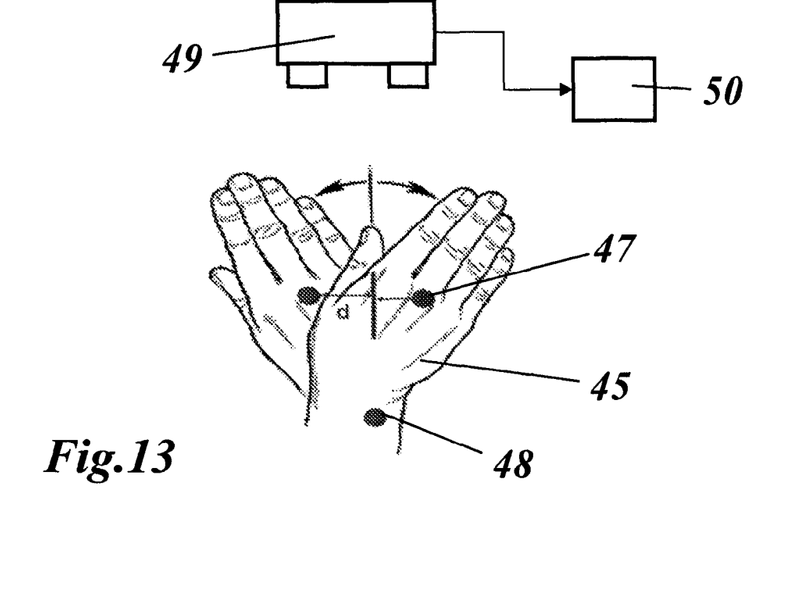
FIG. 13 is a schematic block diagram of a measuring device for quantifying the mobility of a splinted body part.

For this purpose, a forearm was seated semicircularly in a U-shaped splint, and was fastened by textile bandage and, alternatively, by fastening elements according to the present invention. A first ultrasonic marker 47 was arranged in the area of the wrist, on the back of the hand, as shown in FIG. 13, and a second ultrasonic marker 47 was arranged on the forearm, for transmitting ultrasonic impulses to an evaluating unit 50 via a receiver 49, for the analysis of the three-dimensional motion of the hand 45. Such a measurement system for real-time analysis of three-dimensional movements on the field of sport and medicine is available in the market, for example the Compact Measurement Systems (CMS) of Zebris Medical GmbH (Germany).

Figure 14:
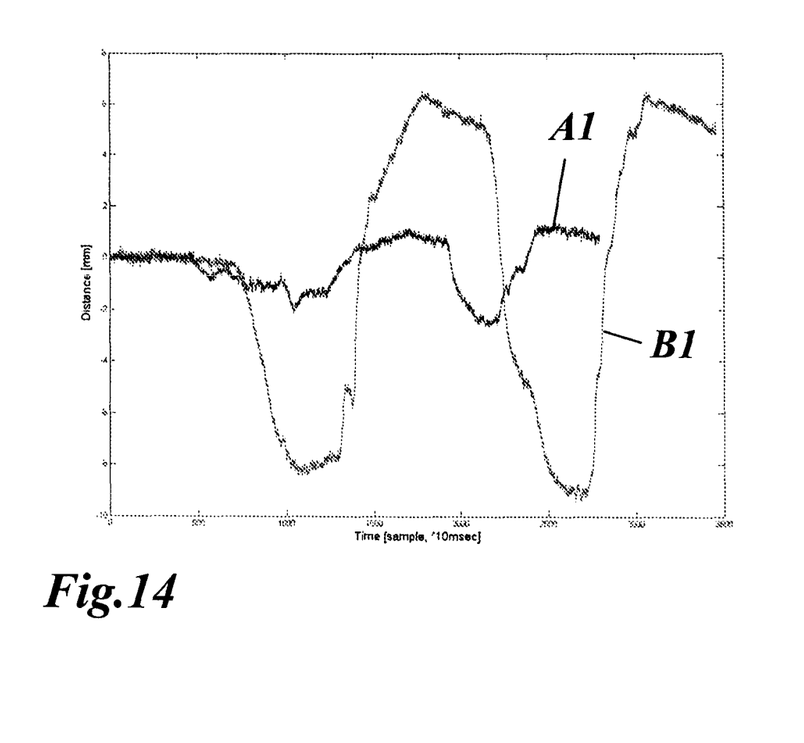
FIG. 14 is a diagram showing the flexion and extension of a wrist joint in a long palmar forearm splint fastened by conventional flexible textile fastening elements (curve B1) and by the fastening elements according to the invention (curve A1), measured by the device shown in FIG. 13.
Figure 15:
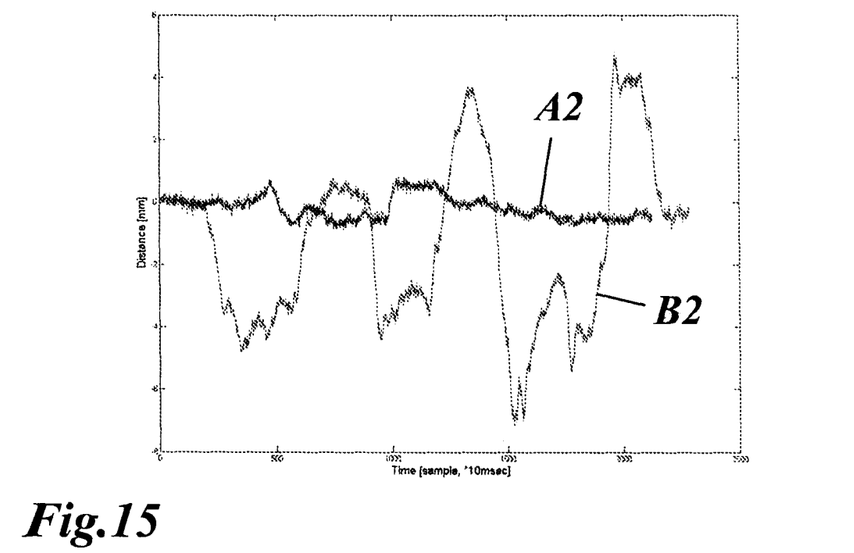
FIG. 15 is a diagram showing the lateral flexion of a wrist joint in a palmar forearm splint fastened by conventional flexible textile fastening elements (curve B2) and by the fastening elements according to the invention (curve A2), measured by the device shown in FIG. 13.
Figure 16:
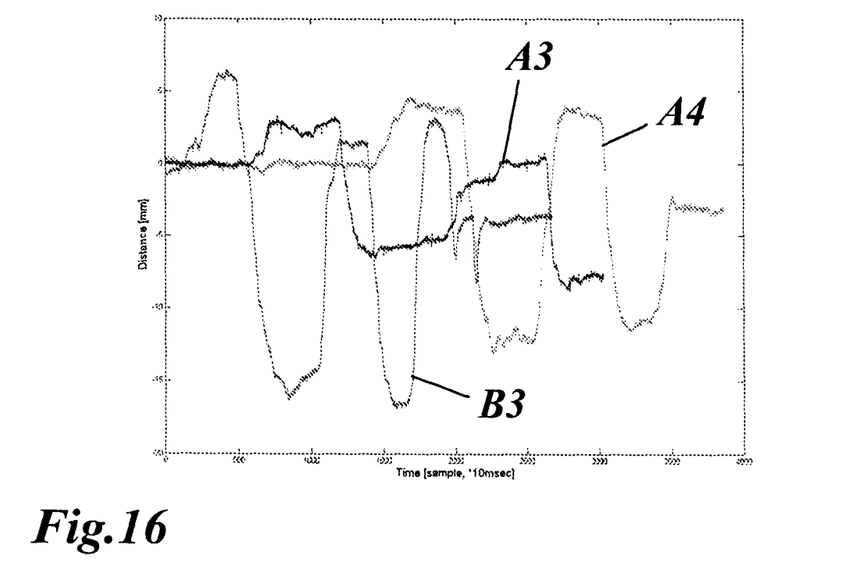
FIG. 16 is a diagram showing the lateral flexion and extension of a wrist joint in a palmar forearm splint fastened by conventional flexible textile fastening elements (curve B3) and by various fastening elements according to the invention (curves A3, A4), measured by the device shown in FIG. 13.

As a measure of the immobilization effect, the radial and ulnar displacement (line 'd' in FIG. 13) was recorded during the reciprocating movement of the hand 45 for different types of splinting. FIGS. 14-16 are graphs showing the displacements of line 'd' in different splints over the time.

Curves A1-A4 show the deflection when using the fastening elements according to the invention, while curves B1-B3 show the deflection when using conventional textile bandages.

The curves in FIG. 14 show the flexion and extension in a long wrist joint splint.

The curves in FIG. 15 show the lateral flexion in a palmar forearm splint.

The curves in FIG. 16 also relate to a palmar forearm splint, wherein the fastening elements were provided with reinforcing strips made of aluminum, having different thicknesses. Curve A3 shows the results with an aluminum plate having the thickness of 1.2 mm, while curve A4 shows the results with an aluminum plate having the thickness of 0.6 mm. The above embodiments clearly prove that applying the fastening elements according to the invention results in a significant improvement in reliable fastening of splinted body parts, wherein the degree of fastening also depends on the feature of the fastening elements.

What I claim is:

1. A fastening element
   formed as a flat, elongated strap and comprising a rigid, yet manually deformable, corrugated metal plate,
   said fastening element having a longitudinal axis and two longitudinally opposite end portions,
   said longitudinal axis extending in a direction along which the fastening element is to be tensioned onto or around an object,
   wherein all of the corrugations of the fastening element are arranged substantially parallel to the longitudinal axis of the fastening element, and
   wherein the corrugated metal plate is provided on both faces thereof with an external covering layer and at least at its longitudinally opposite end portions, with means for releasably attaching the fastening element on or around said object.

2. The fastening element as claimed in claim 1, wherein the corrugated metal plate is made of aluminium.

3. The fastening element as claimed in claim 2, wherein the corrugated metal plate has a thickness of 0.2-1.2 mm.

4. The fastening element as claimed in claim 1, wherein said attaching means include hook and loop fasteners.

5. The fastening element as claimed in claim 1, wherein the external covering layers are made of a flexible material selected from the group of textile and foam.

6. A device for immobilizing an object, the device comprising a stable support for holding an object and at least one fastening element,
   wherein said at least one fastening element is formed as a flat, elongated strap and comprises a rigid, yet manually deformable, corrugated metal plate, and further has a longitudinal axis and two longitudinally opposite end portions,
   said longitudinal axis extending in a direction along which the fastening element is to be tensioned onto or around said stable support,
   wherein the corrugations of the metal plate are arranged substantially parallel to the longitudinal axis of the fastening element,
   wherein the corrugated metal plate is provided on both faces thereof with an external covering layer and at least at its longitudinally opposite end portions, with means for releasably attaching the fastening element to said support for immobilizing the object held by the support, and
   wherein said support comprises counterpart attaching means adapted for coupling with the attaching means of the at least one fastening element.

7. The device as claimed in claim 6, wherein the support is a medical splint.

8. A method of immobilizing a body part by using a fastening element,
   wherein the fastening element is formed as a flat, elongated strap and comprises a rigid, yet manually deformable, corrugated metal plate,
   said fastening element having a longitudinal axis and two longitudinally opposite end portions,
   said longitudinal axis extending in a direction along which the fastening element is to be tensioned onto or around an object,
   wherein the corrugations of the metal plate are arranged substantially parallel to the longitudinal axis of the fastening element, and
   wherein the corrugated metal plate is provided on both faces thereof with an external covering layer and at least at its longitudinal end portions, with means for releasably attaching the fastening element on or around said object, the method comprising:

winding said fastening element around a body to form a helical winding for keeping the body in place.

9. The method of claim 8, wherein the helically wound fastening element is held in a predetermined configuration by reinforcing elements applied externally on the helical winding.

10. The method of claim 8, wherein the body is a finger and the fastening element is helically wound around the finger.

* * * * *